United States Patent [19]
Brown et al.

[11] 3,991,064
[45] Nov. 9, 1976

[54] BENZONAPHTHYRIDINES

[75] Inventors: Richard E. Brown, East Hanover; Chester Puchalski, Dover; John Shavel, Jr., Mendham, all of N.J.

[73] Assignee: Warner-Lambert Company, Morris Plains, N.J.

[22] Filed: Jan. 17, 1975

[21] Appl. No.: 541,912

[52] U.S. Cl. .................. 260/288 CF; 260/243 B; 260/247.2 R; 260/247.5 GP; 260/268 TR; 260/283 S; 260/287 CF; 424/246; 424/248; 424/250; 424/258
[51] Int. Cl.² .................................... C07D 471/04
[58] Field of Search .................. 260/288 CF, 286 R

[56] References Cited
UNITED STATES PATENTS
2,467,692   4/1949   Petrow et al. ................. 260/288 CF

*Primary Examiner*—R. J. Gallagher
*Assistant Examiner*—Mary C. Vaughn
*Attorney, Agent, or Firm*—Albert H. Graddis; Frank S. Chow; George M. Yahwak

[57] ABSTRACT

This invention relates to novel substituted benzo[c][2,7]naphthyridines and their preparation. The compounds of this invention are active as bronchodilators.

8 Claims, No Drawings

BENZONAPHTHYRIDINES

This invention relates to novel substituted benzo[c][2,7] naphthyridines of the following general structure:

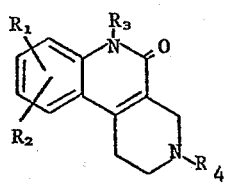

In the above formula, $R_1$ and $R_2$ may be hydrogen or lower alkyl or lower alkoxy of 1 to 6 carbon atoms or taken together may be a methylenedioxy group. $R_3$ and $R_4$ may be hydrogen, lower alkyl, or lower acyl of 1 to 6 carbon atoms, benzoyl, or an ω-cycloalkyl - lower alkyl substitutent of the formula:

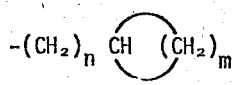

wherein, $m$ is 4 to 6 and $n$ is 2 to 4; or an ω-aminoalkyl substituent of the formula:

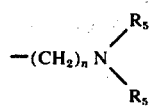

wherein $n$ may be 2 to 4 and $R_5$ may be hydrogen, lower alkyl of 1 to 6 carbon atoms or may, together with the nitrogen atom to which they are attached form the formula:

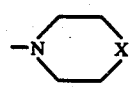

wherein $x$ may be O, S, —CH$_2$—CH$_2$, a bond connecting the adjacent carbon atoms or >CH—R$_6$ >N—R$_6$ wherein $R_6$ may be hydrogen or lower alkyl of 1 to 5 carbon atoms.

The products of this invention are prepared according to the following sequence. In the first step, a substituted aniline derivative according to the formula II is reacted with phosgene to give the isocyanate III. In both formulas II and III, $R_1$ and $R_2$ are as previously defined for structure I.

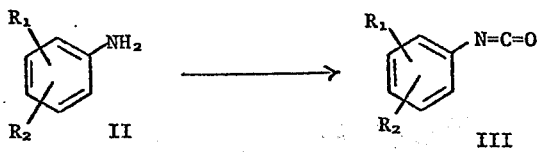

In the second step, the isocyanate according to structure III is reacted with an enamine of N-benzoyl-4-piperidone according to structure IV to give, after acid hydrolysis, an amide according to structure V. Representative enamines of N-benzoyl-4-piperidone which may be used are those from pyrrolidine, morpholine and piperidine.

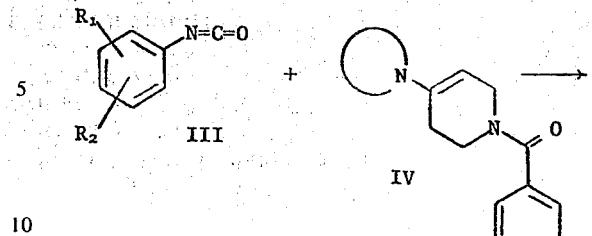

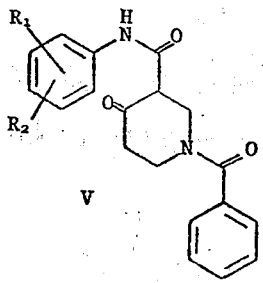

In the third step of the sequence, the compound according to structure V is reacted with an acidic cyclizing agent to give a product according to structure VI. Among the agents which may be used in the cyclization step are polyphosphoric acid, phosphorous oxychloride, or preferably sulfuric acid. Alternatively, the total crude product from reaction

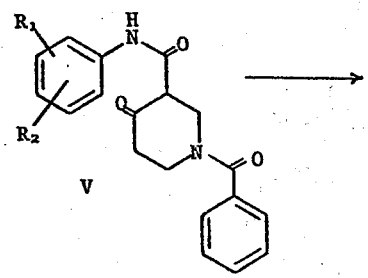

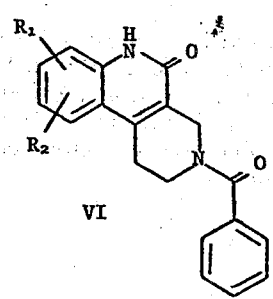

of III and IV may be treated with the acidic cyclizing agent to afford VI directly and thereby avoid isolation of intermediate V.

From intermediate VI, several reaction courses may be followed depending on the substitution desired in the final product I. If it is desired to substitute on the nitrogen atom of ring B, intermediate VI is reacted with a strong base to remove the proton on this nitrogen, and the resulting salt may then be alkylated with the appropriate alkyl halide in a suitable solvent. Among the strong bases which may be used for proton removal in this step are sodium methoxide or ethoxide, potassium t-butoxide, or preferably, sodium hydride. Among the solvents which may be used are tetrahydrofuran, dimethylsulfoxide, or, preferably, dimethylformamide. Among the alkylating agents which may be used to provide the desired substitution on the ring B nitrogen according to the definition of $R_3$ as given for structure I are the chlorides, bromides and iodides of 1 to 6 carbon alkanes and halides according to the formulae VIIa and VIIb:

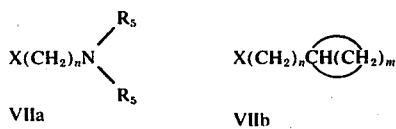

wherein X is a halogen atom and $R_5$, $m$ and $n$ are as defined for structure I.

The product of such an alkylation has the formula VIII, and may be

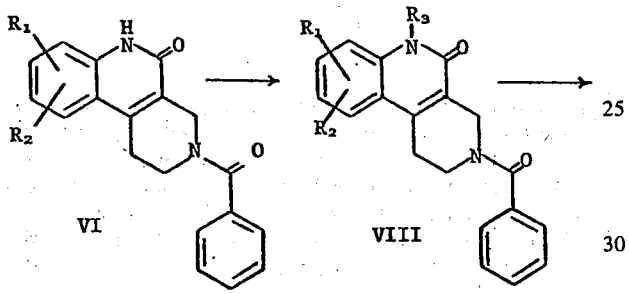

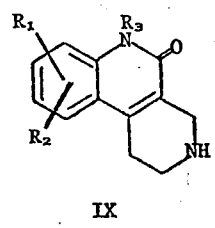

converted to the product of structure IX by hydrolysis with a dilute mineral acid such as hydrochloric or preferably sulfuric acid. It it is desired to substitute on the nitrogen atom of ring C, intermediate VI is hydrolyzed with acid as described above to give a compound according to structure X.

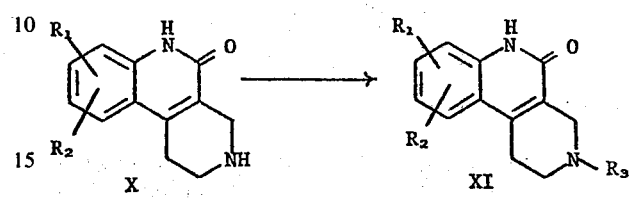

Compound X may be alkylated according to standard procedures without a strong base, because of the basicity of the ring C nitrogen, to give a compound according to structure XI. Among the alkylating agents which may be used are those defined above for the alkylation of VI to VIII.

In the final step, compounds according to IX may be alkylated exactly as described for the conversion of X to XI and with the previously defined alkylating agents to afford products according to structure I.

The following examples are given to allow a further understanding of the invention.

EXAMPLE 1

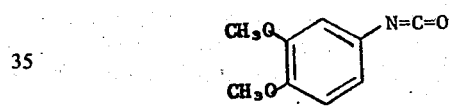

3,4-Dimethoxyphenylisocyanate.

A solution of 0.163 m of 4-aminoveratrole in 250 ml of chlorobenzene was treated with excess HCl gas resulting in a heavy precipitate. The mixture was refluxed and treated with a stream of phosgene for ½ hr (50 g, 0.49 m). After refluxing an additional ½ hr chlorobenzene was evaporated in vacuo. Distillation of the residue afforded 23 g (79%) b.p. 145°–150° C, 17–18 mm.

Anal. Calcd for $C_9H_9NO_3$: C, 60.33; H, 5.06; N, 7.82. Found: C, 60.63; H, 5.12; N, 7.55.

EXAMPLE 2

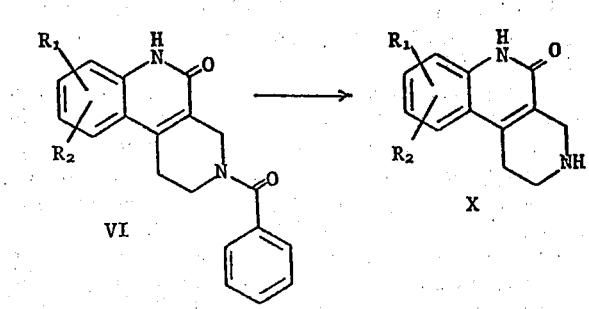

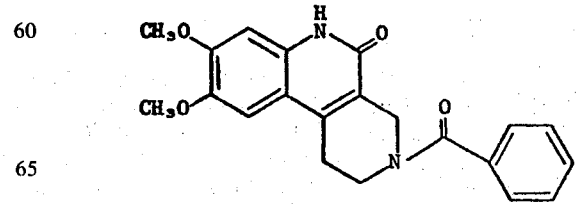

3-Benzoyl-1,2,3,4-Tetrahydro-8,9-Dimethoxybenzo[c][2,7]-naphthyridin-5(6H)-one.

A solution of 47 g (0.262 m) of 3,4-dimethoxyphenylisocyanate in 50 ml of CH$_2$Cl$_2$ was added over 15 min to a stirred solution of 0.262 m of the pyrrolidine enamine of n-benzoyl-4-piperidone in 250 ml of CH$_2$Cl$_2$. The reaction was stirred overnight, then evaporated in vacuo to give the crude amido enamine. This was taken up in 200 ml of MeOH, treated with 60 ml of conc HCl and allowed to stand at room temperature for 5 hr. The reaction was diluted to 1 l. with water and extracted with CHCl$_3$. The CHCl$_3$ extract was crosswashed with water, dried (Na$_2$SO$_4$) and evaporated in vacuo to give the gummy β-keto amide of structure V.

The crude β-keto amide was treated with 100 ml of H$_2$SO$_4$ and heated momentarily on the steam bath. After the exothermic reaction subsided heating was resumed for 10 min. The reaction mixture was poured into 800 g of ice water and stirred. Filtration afforded 55 g of product. Recrystallization from dimethylformamide afforded pure material, mp 290°–297° C.

Anal. Calcd for C$_{21}$H$_{20}$N$_2$O$_4$: C, 69.21; H, 5.53; N, 7.69. Found: C, 69.12; H, 5.47; N, 7.52.

EXAMPLE 3

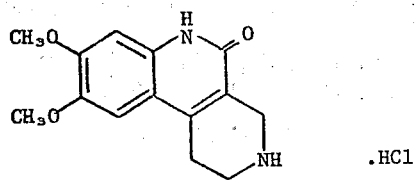

1,2,3,4-Tetrahydro-8,9-dimethoxybenzo[c][2,7]naphthyridin-5(6H)-one Hydrochloride.

A solution of 2 g (0.0055 m) of 3-benzoyl-1,2,3,4-tetrahydro-8,9-dimethoxybenzo[c][2,7]naphthyridin-5(6H)-one in 15 ml water, 5 ml H$_2$SO$_4$ and 5 ml 2-propanol was refluxed for 23 hr. The reaction was cooled, made basic with conc NH$_4$OH solution, and the solid was filtered off. Crystallization from 3N HCl afforded pure material, mp 250°–255° C.

Anal. Calcd for C$_{14}$H$_{16}$N$_2$O$_3$.HCl: C, 56.67; H, 5.77; N, 9.44; Cl, 11.95. Found: C, 55.37; H, 5.97; N, 9.16; Cl, 11.82.

EXAMPLE 4

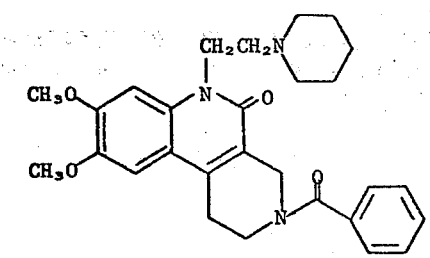

1,2,3,4-Tetrahydro-3-benzoyl-8,9-dimethoxy-6-(2-piperidinoethyl)benzo[c][2,7]naphthyridin-5(6H)-one.

A suspension of 0.066 m NaH in 75 cc dimethylsulfoxide was cooled in a cold water bath and treated portionwise with 10 g (0.028 m) of 3-benzoyl-1,2,3,4-tetrahydro-8,9-dimethoxy-benzo[c][2,7]naphthyridin-5(6H)-one in 10 min. After stirring for 5 min the reaction was treated with 5.5 g (0.03 m) of N-(2-chloroethyl)piperidine hydrochloride in 2 min. After stirring an additional 2 hr the reaction was diluted with water to 800 ml to give 11.5 g of crude solid product, used as is for hydrolysis.

EXAMPLE 5

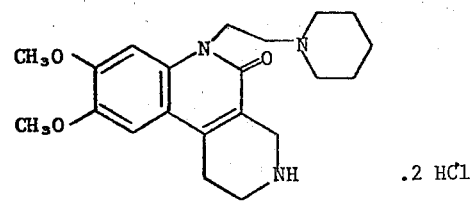

1,2,3,4-Tetrahydro-8,9-dimethoxy-6(2-piperidinoethyl)benzo-[c][2,7]naphthyridin-5(6H)-one dihydrochloride.

A solution of 3.7 g of 1,2,3,4-tetrahydro-3-benzoyl-8,9-dimethoxy-6(2-piperidinoethyl)benzo[c][2,7-]naphthyridin-5(6H)-one in 25 ml of 2-propanol, 5 ml of H$_2$SO$_4$, and 20 ml of water was refluxed for 18 hr. After distilling off the 2-propanol the reaction was washed with two 50 ml portions of ethyl ether, made strongly basic by addition of conc NH$_4$OH, and extracted with two 50 ml portions of chloroform. After drying (Na$_2$SO$_4$) and evaporation, the chloroform soluble material was dissolved in 40 ml of ethanol, and treated with excess HCl gas. The resulting precipitate was crystallized from ethanol/methanol giving 1.0 g (27%) of material, mp 256°–259° C.

Anal. Calcd for C$_{21}$H$_{29}$N$_3$O$_3$.2HCl: C, 56.76; H, 7.03; N, 9.46; Cl, 15.96. Found: C, 54.82; H, 6.97; N, 9.04; Cl, 15.57.

EXAMPLE 6

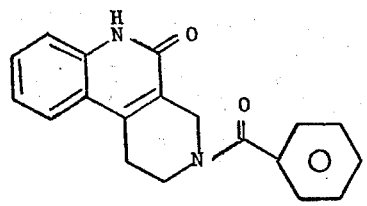

3-Benzoyl-1,2,3,4-tetrahydrobenzo[c][2,7]naphthyridin-5(6H)-one.

In the same way as described in example 2, the title product was prepared starting from phenylisocyanate and the pyrrolidine enamine of N-benzoyl-4-piperidone. Crystallization from methanol afforded analytical material, mp 275°–277° C.

Anal. Calcd for C$_{19}$H$_{16}$N$_2$O$_2$: C, 74.98; H, 5.30; N, 9.21. Found: C, 74.01; H, 5.31; N, 9.15.

EXAMPLE 7

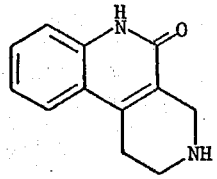

1,2,3,4-Tetrahydrobenzo[c][2,7]naphthyridin-5(6H)-one.

A solution of 7.7 g (0.025 m) of 3-benzoyl-1,2,3,4-tetrahydrobenzo[c][2,7]naphthyridin-5(6H)-one in 30 ml of water, 10 ml of H₂SO₄, and 200 ml of 2-propanol was refluxed for 20 hr. After cooling, the solid was filtered and recrystallized from water, mp 292°–295° C. By analysis, this material contains 0.7 mole of H₂SO₄ per mole of base and was used as is for alkylation.

Anal. Calcd for C₁₂H₁₂N₂O.½H₂SO₄: C, 57.82; H, 5.26; N, 11.24. Found: C, 53.83; H, 5.36; N, 10.12.

EXAMPLE 8

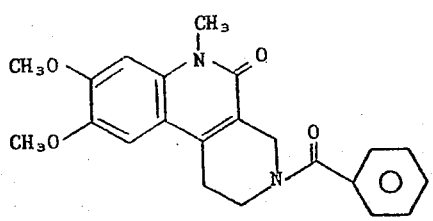

1,2,3,4-Tetrahydro-8,9-dimethoxy-3-benzoyl-6-methylbenzo-[c][2,7]naphthyridin:5(6H)-one.

A stirred suspension of 0.017 m of NaH (washed with petroleum ether) in 50 ml of dimethyl formamide was treated in portions with 5 g (0.0137 m) of 1,2,3,4-tetrahydro-8,9-dimethoxy-3-benzoyl-benzo[c][2,7]naphthyridin-5(6H)-one. After stirring for 10 min, the reaction was treated with 5 g (0.035 m) of CH₃I and stirred an additional 45 min. Dilution with water to 250 ml and filtration gave 4.8 g (93%) of crude material. Crystallization from methanol/CH₂Cl₂ afforded pure material, mp 241°–243° C.

Anal. Calcd for C₂₂H₂₂N₂O₄: C, 69.82; H, 5.86; N, 7.40. Found: C, 68.77; H, 5.90; N, 7.18.

EXAMPLE 9

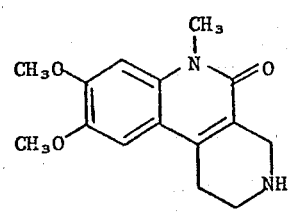

1,2,3,4-Tetrahydro-8,9-dimethoxy-6-methylbenzo[c][2,7]-naphthyridin-5(6H)-one.

In a manner similar to example 3, 1.2g of 1,2,3,4-tetrahydro-8,9-dimethoxy-3-benzoyl-6-methylbenzo[c][2,7]naphthyridin-5(6H)-one was hydrolyzed to give the title compound, mp 178°–179° C after recrystallization from acetonitrile.

Anal. Calcd for C₁₅H₁₈N₂O₃: C, 65.67; H, 6.61; N, 10.21. Found: C, 65.47; H, 6.63; N, 9.92.

EXAMPLE 10

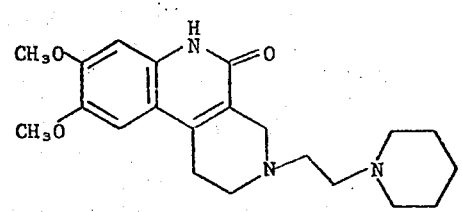

1,2,3,4-Tetrahydro-8,9-dimethoxy-3-(2-piperidinoethyl)-benzo[c][2,7]naphthyridin-5(6H)-one.

A solution of 4.2 g (0.02 m) of 1,2,3,4-tetrahydro-8,9-dimethoxybenzo[c][2,7]naphthyridin-5(6H)-one, 4.05 g (0.022m) of N-(2-chloroethyl)piperidine HCl and 4.45 g (0.044 m) of triethylamine in 125 cc of ethyl alcohol was refluxed for 18 hr. After evaporation, the residue was dissolved in 100 ml of water, made strongly basic with conc NH₄OH solution and extracted with three 50 ml portions of chloroform. The chloroform extract was dried (Na₂SO₄) and evaporated in vacuo. The residue was crystallized from acetonitrile affording 3.3 g (44% of crude material. Recrystallization from 2-propanol afforded analytical material, mp 185°–188° C.

Anal. Calcd for C₂₁H₂₉N₃O₃: C, 67.90; H, 7.87; N, 11.31. Found: C, 67.86; H, 7.73; N, 11.28.

EXAMPLE 11

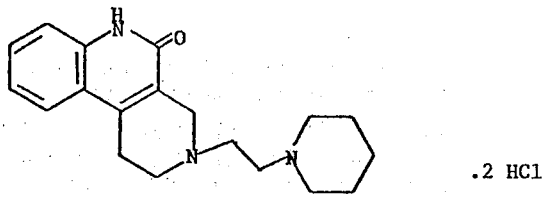

1,2,3,4-Tetrahydro-3-[2-(1-piperidinyl)ethyl]benzo-[c][2,7]naphthyridin-5-(6H)-one .2HCl.

In the same way as described in example 10, 0.02 m of 1,2,3,4-tetrahydrobenzo[c][2,7]naphthyridin-5(6H)-one was alkylated with N-(2-chloroethyl)piperidine HCl. The reaction solution was treated with excess HCl gas affording 2.7 g (35%) of dihydrochloride, mp 265°–268° C.

Anal. Calcd for C₁₉H₂₅N₃O. 2HCl: C, 59.38; H, 7.08; N, 10.93, Cl, 18.45. Found: C, 55.41; H, 6.92; N, 10.14; Cl, 16.48.

EXAMPLE 12

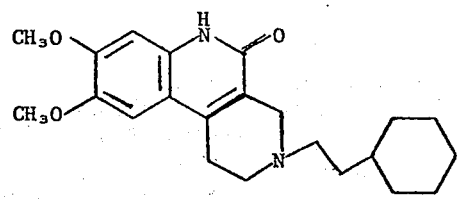

3-(2-Cyclohexylethyl)-1,2,3,4-tetrahydro-8,9-dimethoxy-benzo[c][2,7]naphthyridin-5(6H)-one.

In the same way as described in example 10, 5.2 g (0.02 m) of 1,2,3,4-tetrahydro-8,9-dimethoxybenzo[c][2,7]-naphthyridin-5(6H-one was alkylated with bromoethyl cyclohexane. Crystallization from ethyl acetate afforded 3.5 g (47%) of analytical material, mp 195°-198° C.

Anal. Calcd for $C_{22}H_{30}N_2O_3$: C, 71.32; H, 8.16; N, 7.56. Found: C, 71.06; H, 8.31; N, 7.59.

EXAMPLE 13

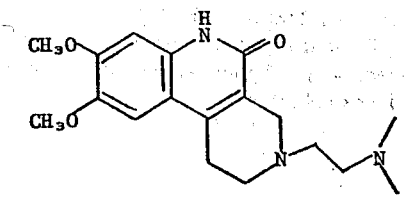

3-[2-(Dimethylamino)ethyl]-1,2,3,4-tetrahydro-8,9-dimethoxybenzo[c][2,7]naphthyridin-5(6H)-one.

In the same way as described in example 10, 0.02 m of 1,2,3,4-tetrahydro-8,9-dimethoxybenzo[c][2,7]-naphthyridin-5(6H)-one was alkylated with dimethylamino ethyl chloride. Crystallization from acetonitrile gave analytical material, mp 160°-164° C.

Anal. Calcd for $C_{18}H_{25}N_3O_3$: C, 65.23; H, 7.60; N, 12.68. Found: C, 64.63; H, 7.39; N, 11.88.

EXAMPLE 14

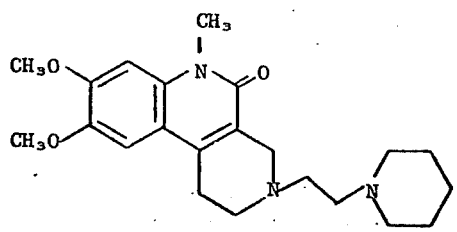

1,2,3,4-Tetrahydro-8,9-dimethoxy-6-methyl-3-(2-piperidino-ethyl)benzo[c][2,7]naphthyridin-5(6H)-one.2HCl.

In the same way as described in example 10, 0.008 m of 1,2,3,4-tetrahydro-8,9-dimethoxy-6-methylbenzo[c][2,7]-naphthyridin-5-(6H)-one was alkylated with N-(2-chloroethyl)piperidine HCl. Treatment of the hot reaction mixture with excess HCl gas afforded crude material. Crystallization from 2-propanol-methanol afforded pure material, mp 234°-240° C.

Anal. Calcd for $C_{22}H_{31}N_3O_3 \cdot 2HCl$: C, 57.64; H, 7.26; N, 9.17; Cl, 15.47. Found: C, 56.40; H, 7.24; N, 8.91; Cl, 15.07.

The compounds of this invention are active as bronchodilators. For example the compound according to the formula:

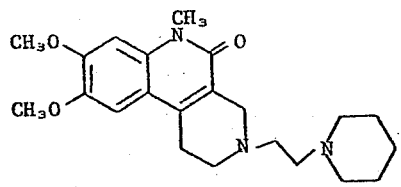

at an IP dose of 3 mg/kg protected the guinea pig against histamine or mecolyl induced bronchospasm for periods up to 4 hours duration.

The compound according to the formula:

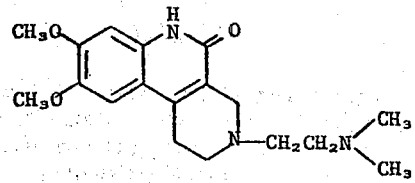

afforded good protection against mecolyl induced bronchospasm in the guinea pig at an IP dose of 25/mg/kg.

The compound according to the formula:

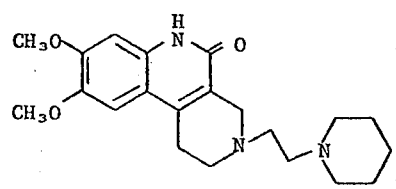

afforded protection against pilocarpine induced bronchospasm in the dog.

We claim:

1. Compounds of the structure:

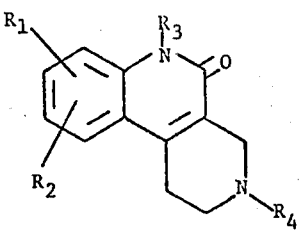

wherein $R_1$ and $R_2$ are hydrogen, lower alkyl, or lower alkoxy of 1 to 6 carbon atoms, or taken together is a methylenedioxy group; $R_3$ is hydrogen, lower alkyl of 1 to 6 carbon atoms and $R_4$ is hydrogen, a ω-cycloalkyl-lower alkyl substituent of the formula:

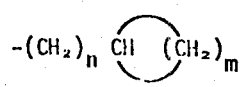

wherein, m is 4 to 6 and n is 2 to 4; or an ω-aminoalkyl substituent of the formula:

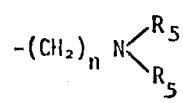

wherein n is 2 to 4, $R_5$ is hydrogen, lower alkyl of 1 to 6 carbon atoms, or together with the nitrogen atom to which they are attached is

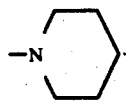

2. Compounds according to claim 1 wherein $R_1$ and $R_2$ are methoxy, $R_3$ is a hydrogen or methyl radical, and $R_4$ is selected from the group consisting of 2-piperidinoethyl, 2-dimethylaminoethyl, and 2-cyclohexylethyl radicals.

3. The compound according to claim 2 wherein $R_3$ is methyl; $R_4$ is 2-piperidinoethyl, and which is 1,2,3,4-tetrahydro-8,9-dimethoxy-6-methyl-3-(2-piperidinoethyl)benzo[c][2,7]naphthydrin-5(6H)-one.

4. The compound according to claim 2 wherein $R_3$ is hydrogen; $R_4$ is 2-dimethylaminoethyl, and which is 3-[2-(dimethylamino)ethyl]-1,2,3,4-tetrahydro-8,9-dimethoxybenzo[c][2,7]naphthyridin-5(6H)-one.

5. The compound according to claim 2 wherein $R_3$ is hydrogen; $R_4$ is 2-cyclohexylethyl, and which is 3-(2-cyclohexyl)-1,2,3,4-tetrahydro-8,9-dimethoxybenzo[c][2,7]naphthyridin-5(6H)-one.

6. The compound according to claim 2 wherein $R_3$ is hydrogen; $R_4$ is 2-piperidinoethyl, and which is 1,2,3,4-tetrahydro-8,9-dimethoxy-3-(2-piperidinoethyl)-benzo[c][2,7]naphthyridin-5(6H)-one.

7. 1,2,3,4-tetrahydro-3-(2-piperidinoethyl)benzo[c][2,7]-naphthyridin-5(6H)-one dihydrochloride.

8. 1,2,3,4-tetrahydro-8,9-dimethoxy-6-(2-piperidinoethyl)benzo[c][2,7]naphthyridin-5(6H)-one dihydrochloride monohydrate.

* * * * *